United States Patent
Tumolo

[11] Patent Number: 5,188,101
[45] Date of Patent: Feb. 23, 1993

[54] PREMATURE BABY HEADBAND FOR SUPPORTING NASAL CANNULAS AND OXYGEN FEED TUBES

[76] Inventor: Jean S. Tumolo, 12 Ash St., Basking Ridge, N.J. 07920

[21] Appl. No.: 792,609

[22] Filed: Nov. 15, 1991

[51] Int. Cl.[5] .................... A61M 15/08; A61M 11/00; A62B 7/00; A42B 1/22

[52] U.S. Cl. .............................. 128/207.18; 128/912; 128/DIG. 26; 128/DIG. 15; 128/101.1; 128/857; 2/DIG. 7; 2/DIG. 11; 2/171.2; 2/183; 604/77; 604/94; 604/179

[58] Field of Search ....................... 128/201.22, 201.26, 128/204.11, 207.18, 911, 912, DIG. 15, DIG. 26, 774, 782, 76 R, 89, 89 A, 97.1, 100.1, 101.1, 857, 877, 163, 169, 171; 604/77, 79, 94, 174, 179, 180, 308, 345; 2/171.2, 183, DIG. 7, DIG. 11

[56] References Cited

U.S. PATENT DOCUMENTS

| | | | |
|---|---|---|---|
| 2,259,817 | 10/1941 | Hawkins | 128/207.18 |
| 4,018,221 | 4/1977 | Rennie | 128/207.18 |
| 4,367,735 | 1/1983 | Dali | 128/207.18 |
| 4,406,283 | 9/1983 | Bir | 128/207.18 |
| 4,641,647 | 2/1987 | Behan | 128/207.18 |
| 4,665,566 | 5/1987 | Garrow | 2/171 |
| 4,671,271 | 6/1987 | Bishop et al. | 128/207.18 |
| 4,774,946 | 10/1988 | Ackerman et al. | 128/207.18 |
| 4,808,160 | 2/1989 | Timmons et al. | 128/207.18 |
| 4,827,923 | 5/1989 | Bishop et al. | 128/207.18 |

*Primary Examiner*—Edgar S. Burr
*Assistant Examiner*—Kimberly L. Asher
*Attorney, Agent, or Firm*—William T. Hough

[57] ABSTRACT

A premature baby elastic strip-like headband having expansion limiting structure with opposite ends of which one end has male hook-like multiple alternate attaching elements and of which a remaining opposite end has female loop-like attaching elements detachably securable to one-another at optionally alternate locations thereof, and having nasal cannulas oxygen tubes-securing structures positioned and mounted on the headband such that the nasal cannulas oxygen tubes are located on opposite side of a baby's head the headband is mounted thereof.

30 Claims, 3 Drawing Sheets

PREMATURE BABY HEADBAND FOR SUPPORTING NASAL CANNULAS AND OXYGEN FEED TUBES

This invention relates to a novel head band specifically designed for use on premature babies, for the mounting of nasal cannulas and opposite oxygen feed tubes thereof.

PRIOR ART

While no relevant prior art was located in a preliminary patentability novelty search that was conducted in Class 128, sub-classes 207.17, 107.18 912, and DIG. 26, patents of mere interest are as follow: U.S. Pat. No. 4,665,566 granted May 19, 1987 to Garrow relating to a headband directed to a substantially common usage to that of the present invention, in mounting of dual spaced-apart nasal oxygen cannulas, but differing in material ways from the present invention; U.S. Pat. No. 4,774,946 granted Oct. 4, 1988 to Ackerman relating likewise to a substantially common head cap usage as that of the present invention, in the mounting of dual spaced-apart nasal oxygen cannulas.

BACKGROUND TO THE INVENTION

Premature babies typically are arching and irritable, not getting adequate rest because of the constant necessity to refit cannula prongs into the nares of the nostrils. It is clearly desirable that the prongs, once finally correctly inserted and positioned, not require future repositioning that often results from slippage and/or shifting with inadequate and/or unstable securing of the oxygen-providing tubes normally placed/mounted on opposite sides of the head.

The present inventor, having been impressed with the commercialized headband disclosed by the above-noted Ackerman patent, became frustrated with the securing mechanism thereof—finding that the premature babies characteristically being writhing, restless and twisting beings, quickly and repeatedly caused the spaced-apart oxygen-providing tubes to pull-out from the laterally-positioned mounting u-shaped members—with the result that the critically required oxygen needed on a constant basis of delivery through the cannulas supported by the tubes was not meeting or even approaching minimum requirements of the patient premature babies. While redundant to so state, it should be apparent that the stable and secure mounting of the two spaced-apart oxygen-providing tubes is directed to the sole or at-least dominant support-purpose for maintaining the cannulas in an inserted state within the nostrils of a premature baby. The cap-like headband slips and slides and/or falls off of the squirming premature babies, resulting in disengagement from and/or incorrectly positioning of the cannulas in the nostrils. It is for this reason that the present invention came into being. While the above-noted Ackerman band and tube and cannulas support might well be satisfactory for a sedimentary non-moving normal non-premature baby or child, such is not the case for the premature babies to which the present invention is directed and has been successfully tested in actual ward use on numerous premature babies. In the hospital wards, attempts have also been made to anchor the spaced-apart oxygen tubes by binding them between opposing strips of material having detachably mateable hooks and loops, of the nature described in the Garrow patent, but with the poor results of the mated-latching thereof being promptly or quickly pulled-apart as a result of the wiggling, squirming and/or writhing of the premature babies having cannulas mounted in their nostrils—with the cannulas according usually quickly falling from and/or being inoperatively repositioned in the nostrils. The hat carrying the loops and hooks arrangements were too loose and the hat did not maintain its shape. Also tube strips thereof come off, releasing the tube(s). Also, extensive efforts have been made by ward nurses and/or attendants to use various combinations of adhesive tape strips, with repeated failures thereof to effectuate any lasting holding and/or supporting of the spaced-apart oxygen-providing tubes and/or the support of the cannulas in fixed proper positioning within the nostrils of the premature baby. In despiration attempts to stabilize and prevent loosening of the support for the oxygen-providing tubes and nasal cannulas supported thereby, the attending staff, tending to the premature babies, turned to use of pins and elastic bands to secure the tubing—together with the accompanying hazard of pins accidentially opening in the vicinity of the infant's eyes or otherwise puncturing the skin. Other persons have attempted to wrap gauze around the premature infant's head together with the anchoring thereof with pins and/or adhesive, elastic bands and the like, all with equal unsatisfactory and/or failing results.

OBJECTS OF THE INVENTION

Accordingly, objects of the present invention include the overcoming of difficulties and problems above-discussed in the maintaining of sturdy and lasting intermittent attachment and support of oxygen-providing tube(s) and nasal cannulas supported thereby within the nostrils of premature babies, with a resultant loss of life and/or avoidance of brain or other cellular damage otherwise arising from a shortage of oxygen. While elastic banded headbands have been used in certain instances, the tightness thereof is dangerous to the pliable underdeveloped heads of premature babies, together with potentially further cutting-off desired and/or essential blood circulation (and oxygen content thereof) to vital head parts; and together with the realistic possibility of disfiguring the tender and underdeveloped heads of such premature babies.

Another particular object is to provide a novel headband that is not readily subject to slip-off of the head of a baby on which it is mounted in the support of oxygen-providing tubes that support nasal cannulas within the nostrils of a premature baby.

Another object is to provide a novel headband devoid of potential damage to the circulation and/or pliable form of the head of a premature infant baby, when mounted thereon.

Another object is to obtain a headband for sturdy mounting of oxygen-providing tubes and resulting support of nasal-inserted cannulas, while achieving simplicity of intermittent securing of oxygen-providing tubes and nasal cannulas supported thereby.

Another object is to obtain a headband of simple and inexpensive structure adapted for sturdy intermittent mounting and support of oxygen-providing tubes that support nasal cannulas.

Another object is to obtain a headband adaptable to easy and quick intermittent mounting and dismounting from the head of a premature baby, for the secure supporting of oxygen-providing tubes that support nasal cannulas.

Another object is to provide a novel support for oxygen-providing tubes utilized to support nasal cannulas for premature babies, while concurrently leaving ample free space facilitating better and/or improved access for peripheral IVs, arterial lines and percutaneous lines.

Other objects become apparent from the preceding and following disclosure.

BROAD DESCRIPTION

Broadly the invention may be described as a premature baby headband device for supporting nasal cannulas and opposite air and/or oxygen tubes, comprises a combination, as follows. Headband structure(s) and mechanism(s) thereof have a longitudinal length for exerting a predetermined degree of stretchable and retractable elasticity. The headband and mechanism thereof include first and second mateable securing means. The headband structure(s) and mechanism thereof include an elongated substantially flat-faced band having opposite first and second ends. The first end mounts the first mateable securing structure(s) and mechanism thereof. The second end mounts the second mateable securing structure(s) and mechanism thereof. The first and second mateable securing structure(s) and mechanism(s) thereof are intermittently alternately securable to and releasable from one-another. The first and second securing structure(s) and mechanism(s) have alternately available positions for securing the above-noted opposite first and second ends and for securing and releasing the above-noted first and second ends alternately at the alternately available positions. The headband has at-least a minor amount of flexibility for resilient alternate stretch and retraction during mounting of the headband on and circumscribingly around an upper head and forehead of a premature patient child. The headband has an elongated axis along the longitudinal length. There are stretch-limiting structure(s) and mechanism thereof having an elongated shape for mounting along said longitudinal length. The stretch-limiting structure(s) and mechanisms thereof are mounted on and secured to said headband at multiple points along the longitudinal shape and the longitudinal length such that the stretch-limiting means is further for preventing the headband means from excessive stretching beyond a predetermined degree and amount of permissive stretching along said longitudinal length, thereby excessive band tightness during band resilient retraction is avoided when mounted on a baby's head. Additionally there are nasal-cannulas oxygen tubes-securing structure(s) and mechanism thereof for intermittent securing and releasing each of at-least two spaced-apart oxygen-providing tubes connected to the nasal cannulas. The nasal cannulas oxygen tubes-securing structure(s) and mechanism thereof is/are mounted on the headband structure(s) and mechanism thereof.

In an alternate second broad embodiment, the premature baby headband device for supporting nasal cannulas and opposite air and/or oxygen tubes, as a combination may be described as follows. There are annular headband structure(s) and mechanism thereof for fitting downwardly circumscribingly around and upon a premature baby's head. The headband structure(s) and mechanism thereof have a longitudinal length for exerting a predetermined degree of stretchable and retractable elasticity. The headband includes an elongated substantially flat-faced band or strip that has at-least a minor amount of flexibility for resilient alternate stretch and retraction during mounting of the annular headband on and circumscribingly around an upper head and forehead of a premature patient child. The headband has an elongated axis along said longitudinal length. There is stretch-limiting structure and mechanism thereof having an elongated shape for mounting along the longitudinal length. The stretch-limiting structure(s) and mechanism thereof are mounted on and secured to the headband at multiple points along the longitudinal shape and the longitudinal length such that the stretch-limiting means is further for preventing the headband means from excessive stretching beyond a predetermined degree and amount of permissive stretching along the longitudinal length. Thereby excessive band tightness during band resilient retraction is avoided when mounted on a premature baby's head. And nasal cannulas oxygen tubes-securing structure(s) and mechanism are provided for intermittent securing and releasing each of at least two spaced-apart oxygen-providing tubes connected to the nasal cannulas. The nasal cannulas oxygen tubes-securing structure(s) and mechanism thereof is/are mounted on the headband structure(s) and mechanism thereof.

In a first preferred embodiment on each of the above-described alternate broad statements of the invention, the structure and mechanism thereof that secure the nasal cannulas oxygen and/or air-providing tubes include at least two spaced-apart tying structure(s) and mechanism thereof. At least one of the tying structure(s) and mechanism thereof includes loose-ends of predetermined lengths sufficient for the loose ends to jointly envelope and be tied-together to secure at least that one of the normally two spaced-apart oxygen-providing tubes, preferably securing both. One of the spaced-apart tying structure(s) and mechanism thereof is positioned to be mounted adjacent one side of a baby's head and a remaining other one of the spaced-apart tying structure(s) and mechanism thereof is positioned on an opposite other side of a baby's head, when the headband structure(s) and mechanism thereof are mounted on a premature baby's head.

In a second preferred embodiment as an improvement on the above-described first preferred embodiment, each of the above-noted loose-ends includes an elongated ribbon-shaped composition adapted for two of the elongated ribbon-shaped compositions to be tied together for each pair or set of above-noted loose-end, when a set of loose-ends is jointly enveloping one of the two spaced-apart oxygen-providing tubes.

In a third preferred embodiment as an improvement on the above-described second preferred embodiment, the stretch-limiting structure(s) and mechanism thereof include a plurality of serially-positioned end-to-end strips of the elongated composition. The loose-ends are end-portions of the end-to-end strips. The stretch-limiting structure(s) and mechanism thereof include the nasal cannulas oxygen-providing tubes-securing structure(s) and mechanism thereof.

In a fourth preferred embodiment as an improvement on the third preferred embodiment, the stretch-limiting structure(s) and mechanism thereof consist essentially of close-knitted elongated ribbon-like strips.

In a fifth preferred embodiment as an improvement on the fourth preferred embodiment, the headband structure(s) and mechanism thereof comprise elastic ace-bandage.

In a sixth preferred embodiment as an improvement on the fourth preferred embodiment, the headband structure(s) and mechanism thereof includes laminated elastic bandage laminated by an intermediate binding composition.

In a seventh preferred embodiment as an improvement on the sixth preferred embodiment, the intermediate binding composition comprises latex composition.

In an eighth preferred embodiment as an improvement on the eighth preferred embodiment, the loose-ends each range in length from about 7 centimeters to about 20 centimenters in length, and each have a width ranging from about 0.6 centimeter to about 2 centimeters.

In a ninth preferred embodiment as an improvement on the ninth preferred embodiment, the loose-ends each range in length from about 10 centimeters to about 15 centimeters in length, and each have a width ranging from about 1 centimeter up to about 1.5 centimeters.

In a tenth preferred embodiment as an improvement on the ninth preferred embodiment, the headband means ranges in length from about 18 centimeters to about 45 centimeters.

In an eleventh preferred embodiment as an improvement on the tenth preferred embodiment, the headband means ranges in length from about 21 centimeters to about 24 centimeters.

In a twelfth preferred embodiment as an improvement on the eleventh preferred embodiment, the headband means ranges in length from about 25 centimeters to about 28 centimeters.

In a thirteenth preferred embodiment as an improvement on the twelfth preferred embodiment, the headband means ranges in length from about 29 centimeters to about 32 centimeters.

In a fourteenth preferred embodiment as an improvement on the thirteenth preferred embodiment, the headband means ranges in length from about 33 centimeters to about 36 centimeters.

In a fifteenth preferred embodiment as an improvement on the fourteenth preferred embodiment, the headband means ranges in length from about 37 centimeters to about 40 centimeters.

In a sixteenth preferred embodiment as an improvement on each of the above-described alternate statements of the broad invention, the stretch-limiting structure(s) and mechanism thereof consist essentially of close-knitted elongated ribbon-like strips.

In a seventeenth preferred embodiment as an improvement on each of the above-described alternate statements of the broad invention, the headband structure(s) and mechanism thereof comprise elastic bandage.

In an eighteenth preferred embodiment as an improvement on the first above-described broad invention, the headband structure(s) and mechanism thereof includes laminated elastic bandage laminated by an intermediate binding composition.

In a nineteenth preferred embodiment as an improvement on the eighteenth preferred embodiment, the intermediate binding composition comprises latex composition.

In a twentieth preferred embodiment as an improvement on the first preferred embodiment, the loose-ends each range in length from about 7 centimeters to about 20 centimeters in length, and each have a width ranging from about 0.6 centimeter to about 2 centimeters.

In a twenty-first preferred embodiment as an improvement on the first preferred embodiment, the loose-ends each range in length from about 10 centimeters to about 15 centimeters in length, and each have width ranging from about 1 centimeter up to about 1.5 centimeters.

In a twenty-second preferred embodiment as an improvement on above-described first broad invention, the headband structure(s) and mechanism thereof range in length from about 18 centimeters to about 45 centimeters.

In a twenty-third preferred embodiment as an improvement on the above-described first broad invention, the headband structure(s) and mechanism thereof ranges in length from about 21 centimeters to about 24 centimeters.

In a twenty-fourth preferred embodiment as an improvement on the above-described first broad invention, the headband structure(s) and mechanism thereof range in length from about 25 centimeters to about 28 centimeters.

In a twenty-fifth preferred embodiment as an improvement on the above-described first broad invention, the headband structure(s) and mechanism thereof range in length from about 29 centimeters to about 32 centimeters.

In a twenty-sixth preferred embodiment as an improvement on the above-described first broad invention, the headband structure(s) and mechanism thereof range in length from about 33 centimeters to about 36 centimeters.

In a twenty-seventh preferred embodiment as an improvement on the above-described first broad invention, the headband structure(s) and mechanism thereof range in length from about 37 centimeters to about 40 centimeters.

In a twenty-eighth preferred embodiment of the invention as an improvement on the above-described alternate second broad invention, the annular headband structure(s) and mechanism(s) thereof have an inner circumference ranging from about 18 centimeters to about 45 centimeters.

In another alternate, third broad embodiment, for supporting nasal cannulas and opposite air and/or oxygen tubes, the combination comprises headband structure and mechanism thereof having an elongated dimension and along the elongated dimension having a predetermined degree of stretchable and retractable elasticity. The headband structure in the form of a substantially flat-faced band has at least a minor amount of flexibility for resilient alternate stretch and retraction during mounting of thereof on and circumscribingly around an upper head and forehead of a premature patient child. The elongated dimension has an elongated axis. Stretch-limiting structure and mechanism of elongated shape for mounting along the longitudinal length, are mounted on and secured to the headband structure at multiple points along said longitudinal shape and said longitudinal length such that said stretch-limiting structure and mechanism are further for preventing the headband structure from excessive stretching beyond a predetermined degree and amount of permissive stretching along said longitudinal length whereby excessive band tightness during band resilient retraction is avoided when mounted on a baby's head, and nasal cannulas oxygen tubes-securing structure and mechanism thereof for intermittent securing and releasing each of at least two spaced-apart oxygen-providing tubes connected to nasal cannulas. Cannulas air and/or oxygen tubes-securing structure mountable on the headband structure.

In a twenty-ninth preferred embodiment as an improvement on the generic and third broadly-stated invention, the headband is annular headband structure and has an inner circumference ranging from about 21 centimeters to about 24 centimeters.

In a thirtieth preferred embodiment as an improvement on the generic and third broadly-stated invention, the headband is annular and has an inner circumference ranging from about 25 centimeters to about 28 centimeters.

In a thirty-first preferred embodiment as an improvement on the third broadly embodiment, an annular headband has an inner circumference from about 29 centimeters to about 32 centimeters.

In a thirty-second preferred embodiment as an improvement on the third broad embodiment, an annular headband has an inner circumference from about 33 centimeters to about 36 centimeters.

In a thirty-third preferred embodiment as an improvement on the generic and fourth broadly-stated invention, the headband is annular and has an inner circumference ranging from about 37 centimeters to about 40 centimeters.

The invention may be better understood by making reference to the following figures.

DETAILED DESCRIPTION

Figure 1:
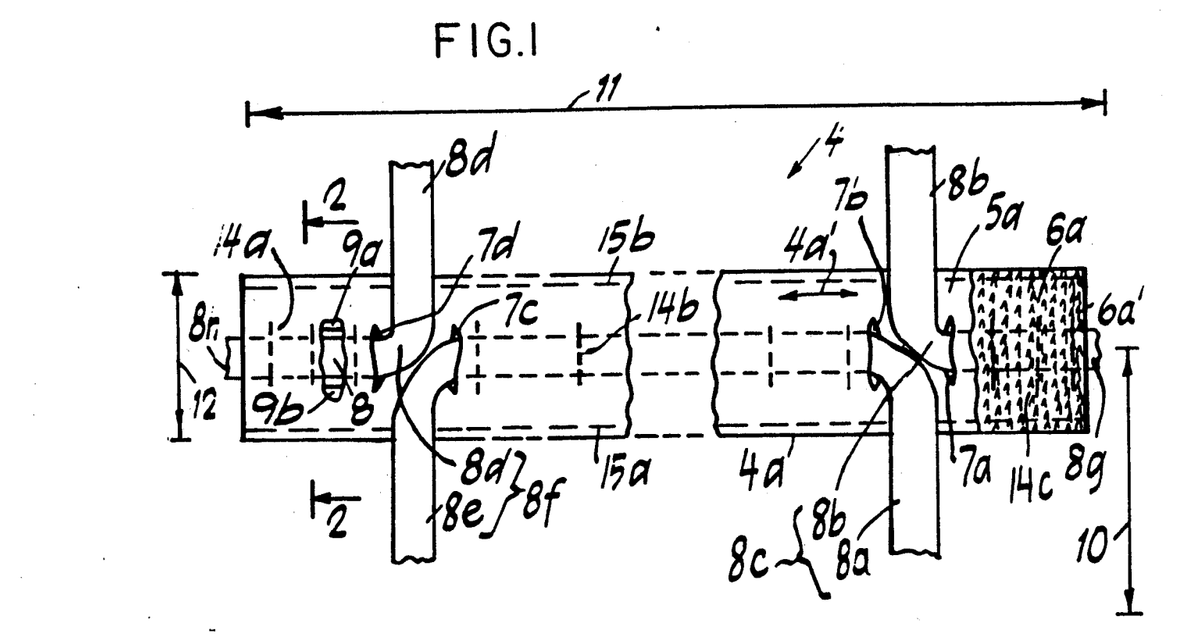
FIG. 1 diagrammatically illustrates a top plan view of the headband device above-described of this invention in a preferred embodiment thereof, with partial cut-away for improved explanation and description, the bottom face appearing the same as the upper face except for the tie-ribbon strips arising from the top face thereof, which normally would constitute the outer-facing face or surface thereof when mounted on a baby's head.
Figure 2:
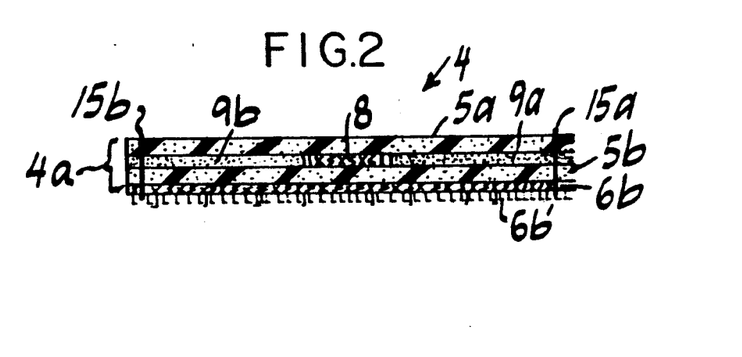
FIG. 2 diagrammatically illustrates a cross-sectional view of the embodiment of FIG. 1, taken along lines 2—2 of FIG. 1, illustrating the laminated layers and stitching and bottom end with mounted (layered) hook-like securing mounting layer and hook-elements arising therefrom.
Figure 3:
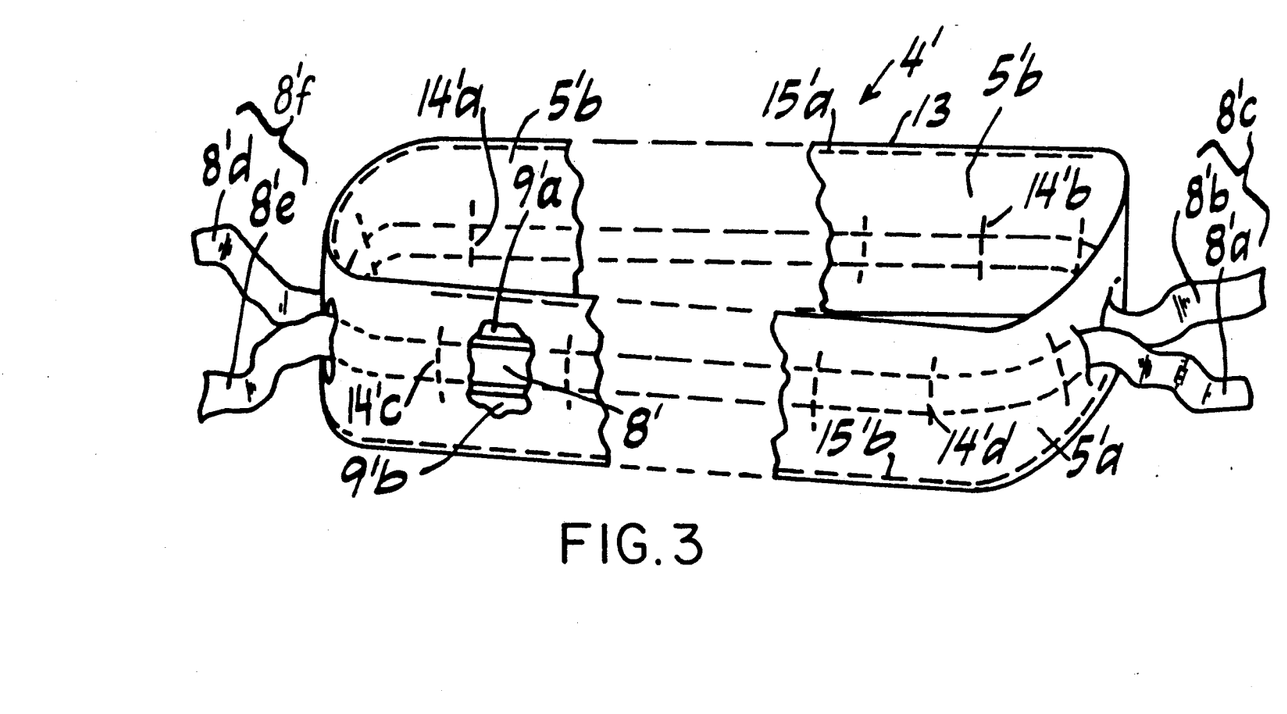
FIG. 3 diagrammatically illustrates an annular headband embodiment of the invention, in a front and top perspective view thereof, having the same laminated layer construction and composition as that illustrated in FIG. 2.

FIGS. 1 and 2 illustrate a common preferred embodiment of the invention and accordingly exhibit correspondingly identical indicia where there is repetition. FIG. 3, illustrating a variation as an annular preferred embodiment, nevertheless otherwise has the same basic construction of laminated parts and compositions and stitching and ribbon strips and the like, and accordingly have correspondingly related indicia for elements corresponding to those to be hereinbelow described for. FIGS. 1 and 2.

Figure 4:
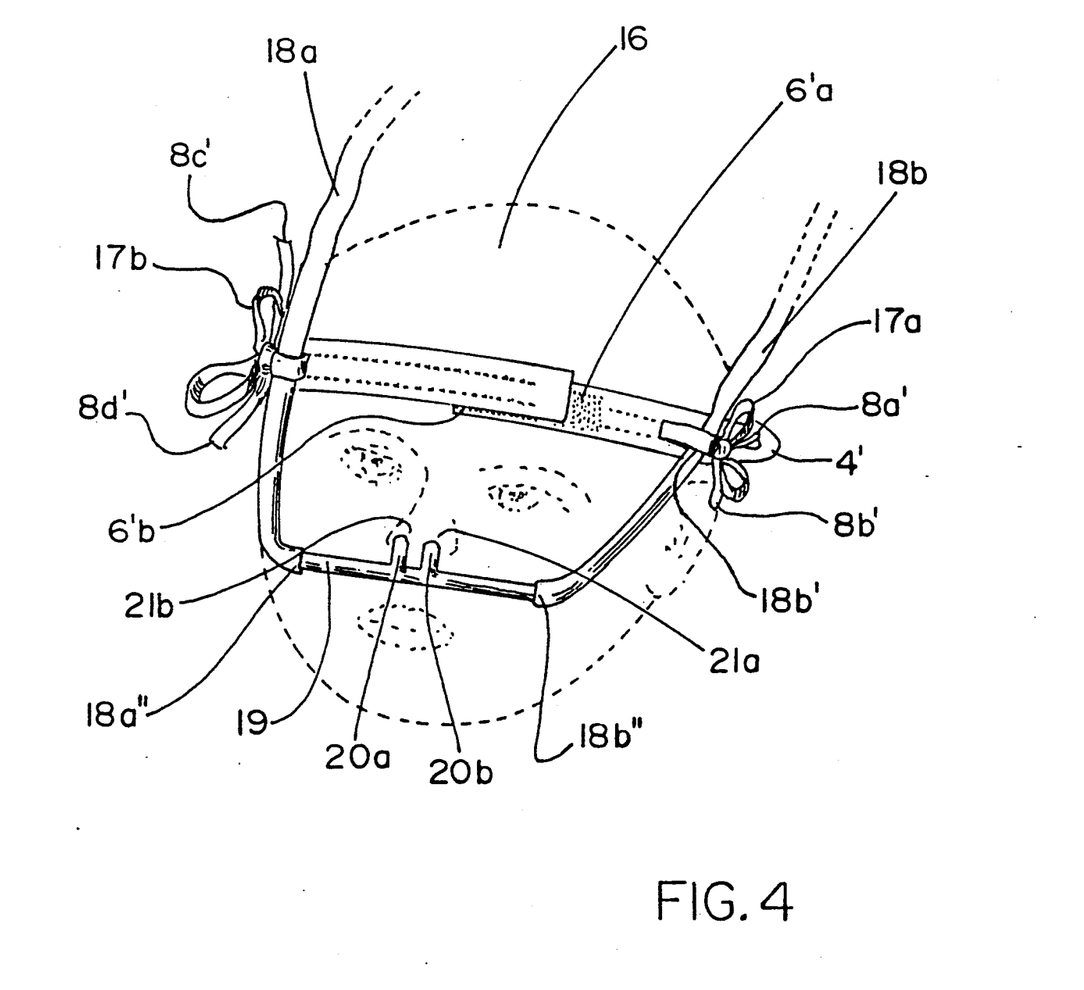
FIG. 4 illustrates the device connected to nasal tubes in position on an infant's head.

Accordingly, FIG. 1 diagrammatically illustrates the lineally-extending embodiment of the headband device 4 of this invention that in use is mounted around the head at the forehead level the same position as is aptly illustrated in each of the above-discussed prior art U.S. Pat. Nos. 4,665,566 to Garrow and 4,774,946 to Ackerman—both patents being herewith incorporated by reference into this disclosure as if fully repeated herein, such positioning being illustrated in FIG. 4.

For the device 4, there is shown the upper face 5a of elastic elongated laminated band 4a having elongated longitudinal axis 4a'. Mounted on one end of that upper face is the loop-elements fabric having female loop elements 6a' extending outwardly therefrom as shown, being concurrently stitched by the same cross-stitchings typically represented by stitching 24c that serves in-part to secure a portion of the ribbon-like strip 8g. The upper surface 5a has a pair of spaced-apart aligned openings 7a and 7b about mid-point of the width thereof as a part of the tying structure at one end of the upper face 5a, and has a second pair of spaced-apart aligned openings 7c and 7d about mid-point of the width as also apart of the tying structure at an opposite end of the upper face 5a. Loose or free tying strip ribbon-end 8a exits through the opening 7a in the upper face at one end, as does the loose tying strip ribbon-end 8b through the opening 7b. Likewise the tying strip 8d exits from opening 7d and tying strip 8e exits from opening 7c of the upper face 5a. Throughout the elastic elongated laminated band 4a is positioned the loosely-laid (not under elongated stretch-stress) serially consecutively aligned non-elastic ribbon-like strips 8 having continuous (integral) therewith the above-identified loose ends 8a, 8b, 8d and 8e. The non-elastic ribbon-like strips 8 are intermittently anchored by cross-stitching 14a, 14b and the like anchoring the ribbon-like strips 8 to the elongated laminated band 4a. In the cut-away of FIG. 1, there are viewable on opposite sides of one of the non-elastic ribbon-like strips 8, the laminating latex 9a and 9b (typically) binding together the upper face 5a and the lower face 5b (see FIG. 2), which are also held in the laminated state by typically elastic thread or non-elastic thread loosely-woven, identified as stitching 15a and 15b extending along and adjacent opposite edges that extend along the elongated longitudinal axis 4a' of the elastic elongated laminated band 4a. The loosely lying non-elastic ribbon-like strips 8 intermittently stitched by stitching 14a and 14b and the like permit stretching of the elastic and thereby resilient elongated laminated band 4a. The elastic elongated laminated band 4a is thus stretchable when mounting on a baby's head at about forehead level, but the extent to which it can be stretched is limited by the non-elastic loosely-lying ribbon-like strips 8 restraining amount of stretching of the elastic elongated laminated band 4a by virtue of the intermittent stitching through the ribbon-like strips 8 and through the elongated ribbon-like strips 8. The loose tying ends 8a, 8b, 8d and 8e each have lengths 10 and widths 8e. Likewise the non-elastic loosely lying ribbon-like strips 8 have the same width 8e, in this preferred embodiment. The elongated device 4 and elastic band 4a have a length 11, and a width 12.

FIG. 2 illustrates the FIG. 1 embodiment as taken in cross-section along lines 2—2, showing the state of lamination of the elastic elongated laminated band 4a through the upper and lower surfaces (layers) 5a and 5b laminated together by latex layer 9a and 9b on each of opposite sides of the illustrated one of the non-elastic loosely lying ribbon-like strips 8. The laminated upper and lower surfaces and latex binder-layer 9a are further sewn together by the afore-stated stitching 15a and 15b. Also stitching 15a and 15b at the end-positioned securing hook elements fabric 16b having its male hook elements 16b' that intermittently interlock with the female hook elements 16a' when overlapped during the mounting of the headband device 4 onto the head of a premature baby.

FIG. 3 diagrammatically illustrates in perspective with partial cut-away an annular headband device of the invention, otherwise identical in the make-up of the laminated band of upper and lower faces (layers) 5'a and 5'b and and ribbon-like strips 8' and the latex binder 9'a and 9'b and the loose typing ends 8'a, 8'b, 8'd and 8'e, and the intermittent stitchings 14'a, 14'b, 14'c, 14'd and the like. The basic difference in this embodiment is that no overlapping ends nor end-securing structures (loops and hooks) are required, yet in this embodiment, minor limited stretching is possible to enable the mounting of an annular headband embodiment of the invention having the approximate same dimensions as the circumference of the head of the baby-patient.

While with the embodiment of FIG. 1 various lengths have to be alternately available for use of children of different head sizes—this being particularly true for the headband devices of this invention because of the greatly restricted permissible stretching in order to avoid excessive retraction (resiliency-return) pressure on the tissues and tender or soft skull of a premature baby, likewise to a possibly greater extent the annular band device embodiment requires even more careful sizing or measuring and matching approximate sizes with approximate baby head diameter, to obtain optimal and most safe results.

Consistent with the objects of the invention, the above-described embodiments as claimed hereinafter, make possible better scalp access and observation for peripheral IVs, arterial lines and percutaneous lines.

Normally in the implementing of use of the embodiment of typically that of FIGS. 1 and 2, for example, the following procedure is followed. Choose the size needed by measuring the baby's head circumference. Thereafter place the headband device around the baby's head as if measuring circumference, and position the oppositely-located ties at temporal areas. Fasten the headband device snugly with the hook and loop overlapping securing-fasteners. Place prongs in the nares and adjust the angle of the circuit tubing to line up with the ties. Then tie the ties tightly around the tubing. Continuous positive airway pressure delivery of oxygen and/or air is now secure. The prongs and tubing will move with the baby whether repositioning the baby or with baby movement. Best positioning, for enhancing neurodevelopment or for achieving optimal pulmonary function, can be realized with this inventive device. When moving a baby in or out of an isolette and/or changing to intermittent use of nasal cannula administration, the attendant leaves the headband device in place; merely untie the ties, move the baby and retie the ties around the circuit tubing and/or nasal cannula.

The above-described construction with its limited minor degree of permissible stretching, with the initial conforming the fit to the infant's scalp dimensions, remains consistant and constant in its limiting of the maximum elasticity of the material of the band and the stretch limiting structure above-discussed and the intermittently stitched ribbon-like strips 8. The fit remains snug, but not harmfully restrictive. The material and construction creates surface tension on the infant's skin, avoiding slipping out of position, but devoid of any substantial risk of excessive elastic-contraction nor of excessive pressure therefrom. The amount of latex is held to a minimum and the elastic fabric of the band is normally a breathable weave that helps to ensure skin integrity and to avoid eventual irritations of the skin.

While male hook-elements and female loop-elements have been illustrated and discussed, it is within the scope and skill of the art to utilize other equivalent fastening means, including tying strings or ribbons, snaps, buttons and the like.

Not only does the inventive device add improved treatment to the premature baby, but by doing so the treated child has longer periods of uninterrupted rest and less nursing time is spent readjusting prongs that heretofore have notoreously slipped-out of the proper positioning and/or nasal cavities to become ineffectual medically or therapeutically. The simplicity of applying the inventive headband device of any illustrated embodiment, facilitates the speedy and proper and frequent use when needed of these devices to the ultimate further and improved benefits of the suffering premature baby's—readily and realistically potentially saving the lives of many premature babies and/or preventing brain or other damage because of lack of adequate oxygen otherwise.

Likewise, it is within the scope of the invention to make any and/or other modifications and/or substitution of equivalents and/or variations within the skill of an artisan of ordinary skill in this particular art.

I claim:

1. A premature baby headband device for supporting nasal cannulas and opposite oxygen feed tubes, comprising in combination: headband means having a longitudinal length for exerting a predetermined degree of stretchable and retractable elasticity, said headband means including first and second mateable securing means, the headband means being an elongated substantially flat-faced band having opposite first and second ends, the first end mounting said first mateable securing means, the second end mounting said second mateable securing means, the first and second mateable securing means being intermittently alternately secureable to and releasable from one-another, said first and second securing means having alternately available positions for securing said opposite first and second ends and securing and releasing said first and second ends alternately at said alternately available positions, said headband means having at-least a minor amount of flexibility for resilient alternate stretch and retraction during mounting of the headband means on and circumscribingly around an upper head and forehead of a premature patient child, said headband means having an elongated axis along said longitudinal length, stretch-limiting means having an elongated shape for mounting along said longitudinal length, said stretch-limiting means being mounted on and secured to said headband means at multiple points along said longitudinal shape and said longitudinal length such that said stretch-limiting means is further for preventing the headband means from excessive stretching beyond a predetermined degree and amount of permissive stretching along said longitudinal length whereby excessive band tightness during band resilient retraction is avoided when mounted on a baby's head, and tube securing means for intermittent securing and releasing each of at-least two spaced-apart oxygen-providing tubes connected to nasal cannulas, said tube securing means being mounted on said headband means, said headband means including an elastic bandage and an intermediate binding composition laminating the elastic bandage and forming as a laminated elastic bandage, said stretch-limiting means consisting essentially of at-least two spaced-apart, close-knitted, elongated, ribbon-like strips embodied within said laminated elastic bandage, and said tube securing means including each of said at-least two spaced-apart opposite loose-ends of said spaced-apart elongated ribbon-like strips each exterior to said laminated elastic bandage, said loose-ends being of predetermined lengths sufficient for paired-ones of said loose-ends to jointly envelope and be tied-together such that each paired-ones are secureable on one of paired spaced-apart nasal cannulas, one of said paired-ones being positioned to be mounted adjacent on one side of a baby's head and a remaining one of said paired-ones being positioned on an other side of a baby's head when the band means is mounted on a premature baby's head.

2. The headband device of claim 1, in which said intermediate binding composition comprises latex composition.

3. The headband device of claim 1, in which said loose-ends each range in length from about 7 centimeters to about 20 centimeters in length, and each have a width ranging from about 0.6 centimeter to about 2 centimeters.

4. The headband device of claim 1, in which said loose-ends each range in length from about 10 centimeters to about 15 centimeters in length, and each have a width ranging from about 1 centimeter up to about 1.5 centimeters.

5. The headband device of claim 1, in which said headband means ranges in length from about 18 centimeters to about 45 centimeters.

6. The headband device of claim 1, in which said headband means ranges in length from about 21 centimeters to about 24 centimeters.

7. The headband device of claim 1, in which said headband means ranges in length from about 25 centimeters to about 28 centimeters.

8. The headband device of claim 1, in which said headband means ranges in length from about 29 centimeters to about 32 centimeters.

9. The headband device of claim 1, in which said headband means ranges in length from about 33 centimeters to about 36 centimeters.

10. The headband device of claim 1, in which said headband means ranges in length from about 37 centimeters to about 40 centimeters.

11. A premature baby headband device for supporting nasal cannulas and opposite oxygen feed tubes comprising in combination: headband means having a longitudinal length for exerting a predetermined degree of stretchable and retractable elasticity, said headband means including first and second mateable securing means, the headband means being an elongated substantially flat-faced band having opposite first and second ends, the first end mounting said first mateable securing means, the second end mounting said second mateable securing means, the first and second mateable securing means being intermittently alternately securable to and releasable from one-another, said first and second securing means having alternately available positions for securing said opposite first and second ends and securing and releasing said first and second ends alternately at said alternately available positions, said headband means having at-least a minor amount of flexibility for resilient alternate stretch and retraction during mounting of the headband means on and circumscribingly around an upper head and forehead of a premature patient child, said headband means having an elongated axis along said longitudinal length, stretch-limiting means having an elongated shape for mounting along said longitudinal length, said stretch-limiting means being mounted on and secured to said headband means at multiple points along said longitudinal shape and said longitudinal length such that said stretch-limiting means is further for preventing the headband means from excessive stretching beyond a predetermined degree and amount of permissive stretching along said longitudinal length whereby excessive band tightness during band resilient retraction is avoided when mounted on a baby's head, and tube securing means for intermittent securing and releasing each of at-least two spaced-apart oxygen-providing tubes connected to nasal cannulas, said tube securing means being mounted on said headband means said tube securing means includes at-least two spaced-apart tying means, at-least one of said tying means comprising loose-ends of predetermined lengths sufficient for said loose ends to jointly envelope and be tied-together to secure said spaced-apart oxygen-providing tubes, one said spaced-apart tying means being positioned to be mounted adjacent one side of a baby's head and a remaining one other of said spaced-apart tying means being positioned on an opposite other side of a baby's head when the band means is mounted on a premature baby's head, each said loose-ends including an elongated ribbon-shaped composition adapted for two of the elongated ribbon-shaped compositions to be tied together when jointly enveloping said spaced-apart oxygen-providing tubes, said stretch-limiting means includes a plurality of serially-positioned end-to-end strips of said elongated composition, and said loose-ends are end-portions of said end-to-end strips, said stretch-limiting means including said nasal cannulas oxygen-providing tubes-securing means.

12. The headband device of claim 11, in which said stretch-limiting means consists essentially of close-knitted elongated ribbon-like strips.

13. The headband device of claim 12, in which said headband means comprises elastic bandage.

14. The headband device of claim 12, in which said headband means includes laminated elastic bandage laminated by an intermediate binding composition.

15. The headband device of claim 11, in which said intermediate binding composition comprises latex composition.

16. The headband device of claim 15, in which said loose-ends each range in length from about 7 centimeters to about 20 centimeters in length, and each have a width ranging from about 0.6 centimeter to about 2 centimeters.

17. The headband device of claim 16, in which said headband means ranges in length from about 18 centimeters to about 45 centimeters.

18. The headband device of claim 16, in which said loose-ends each range in length from about 10 centimeters to about 15 centimeters in length, and each have a width ranging from about 1 centimeter up to about 1.5 centimeters.

19. The headband device of claim 18, in which said headband means ranges in length from about 21 centimeters to about 24 centimeters.

20. The headband device of claim 18, in which said headband means ranges in length from about 25 centimeters to about 28 centimeters.

21. The headband device of claim 18, in which said headband means ranges in length from about 29 centimeters to about 32 centimeters.

22. The headband device of claim 18, in which said headband means ranges in length from about 33 centimeters to about 36 centimeters.

23. The headband device of claim 18, in which said headband means ranges in length from about 37 centimeters to about 40 centimeters.

24. A premature baby headband device for supporting nasal cannulas and opposite oxygen feed tubes, comprising in combination: headband means having an elongated dimension and along the elongated dimension having a predetermined degree of stretchable and retractable elasticity, the headband means being in the form of a substantially flat-faced band having at least a minor amount of flexibility for resilient alternate stretch and retraction during mounting thereof on and circumscribingly around an upper head and forehead of a premature patient child, the elongated dimension having an elongated axis, stretch-limiting means having an elongated shape for mounting along said longitudinal length, said stretch-limiting means being mounted on and secured to said headband means at multiple points along said longitudinal shape and said longitudinal length such that said stretch-limiting means is further for preventing the headband means from excessive stretching beyond a predetermined degree and amount of permissive stretching along said longitudinal length whereby excessive band tightness during band resilient retraction is avoided when mounted on a baby's head, and tube securing means for intermittent securing and releasing at spaced-apart locations each of at-least two spaced-apart oxygen-providing tubes connected to nasal cannulas, said tube securing means being mounted on said headband means having one of said at least two spaced-apart oxygen-providing tubes at each of said spaced-apart locations, said headband means including an elastic bandage and an intermediate binding composition laminating the elastic bandage forming a laminated elastic bandage, one of said tube securing means being positioned to be mounted adjacent on one side of a baby's head and a remaining one of said paired-ones being positioned on an other side of a baby's head when the band means is mounted on a premature baby's head.

25. The premature baby headband device of claim 24, in which said annular headband means had an inner circumference ranging from about 18 centimeters to about 45 centimeters.

26. The headband device of claim 24, in which said headband means is annular in shape and has an inner circumference ranging from about 21 centimeters to about 24 centimeters.

27. The headband device of claim 24, in which said headband means is annular in shape and has an inner circumference ranging from about 25 centimeters to about 28 centimeters.

28. The headband device of claim 24, in which said headband means is annular in shape and has an inner circumference ranging from about 29 centimeters to about 32 centimeters.

29. The headband device of claim 24, in which said headband means is annular in shape and has an inner circumference ranging from about 33 centimeters to about 36 centimeters.

30. The headband device of claim 24, in which said headband means is annular in shape and has an inner circumference ranging from about 37 centimeters to about 40 centimeters.

* * * * *